US011718820B2

(12) United States Patent
Finley et al.

(10) Patent No.: US 11,718,820 B2
(45) Date of Patent: Aug. 8, 2023

(54) GENETICALLY MODIFIED HAPLOID ISSATCHENKIA ORIENTALIS

(71) Applicant: CARGILL, INCORPORATED, Wayzata, MN (US)

(72) Inventors: Kenneth R. Finley, St. Bonifacius, MN (US); Holly Jessen, Chanhassen, MN (US); Erin Kathleen Marasco, Excelsior, MN (US); Thomas William McMullin, Minnetonka, MN (US); Ana Negrete-Raymond, Chanhassen, MN (US); Amit Vas, Minneapolis, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 344 days.

(21) Appl. No.: 16/638,251

(22) PCT Filed: Aug. 2, 2018

(86) PCT No.: PCT/US2018/044998
§ 371 (c)(1),
(2) Date: Feb. 11, 2020

(87) PCT Pub. No.: WO2019/036202
PCT Pub. Date: Feb. 21, 2019

(65) Prior Publication Data
US 2020/0172855 A1 Jun. 4, 2020

Related U.S. Application Data

(60) Provisional application No. 62/546,662, filed on Aug. 17, 2017.

(51) Int. Cl.
| | | |
|---|---|---|
| *C12N 1/14* | (2006.01) | |
| *C12N 1/16* | (2006.01) | |
| *C07K 14/39* | (2006.01) | |
| *C12Q 1/02* | (2006.01) | |

(52) U.S. Cl.
CPC ............... *C12N 1/16* (2013.01); *C07K 14/39* (2013.01); *C12Q 1/025* (2013.01)

(58) Field of Classification Search
None
See application file for complete search history.

(56) References Cited

U.S. PATENT DOCUMENTS

| | | | |
|---|---|---|---|
| 6,852,517 | B1 | 2/2005 | Suthers |
| 8,097,440 | B1 | 1/2012 | Buelter |
| 8,158,404 | B2 | 4/2012 | Lies |
| 8,232,089 | B2 | 7/2012 | Urano |
| 2007/0136889 | A1 | 6/2007 | Inze et al. |
| 2009/0226991 | A1 | 9/2009 | Feldman et al. |
| 2012/0252681 | A1 | 10/2012 | Del Cardayre et al. |
| 2019/0360010 | A1 | 11/2019 | Liao |

FOREIGN PATENT DOCUMENTS

| | | |
|---|---|---|
| WO | 9301299 A1 | 1/1993 |
| WO | 1999014335 A1 | 3/1999 |
| WO | 2000071738 A1 | 11/2000 |
| WO | 2002042471 A2 | 5/2002 |
| WO | 2003049525 A2 | 6/2003 |
| WO | 2003102152 A2 | 12/2003 |
| WO | 2003102201 A2 | 12/2003 |
| WO | 2004000381 A1 | 12/2003 |
| WO | 2004099381 A2 | 11/2004 |
| WO | 2007032792 A2 | 3/2007 |
| WO | 2007106524 A2 | 9/2007 |
| WO | 2007117282 A2 | 10/2007 |
| WO | 2008121701 A1 | 10/2008 |
| WO | 2014018757 A1 | 1/2014 |
| WO | 2014051135 A2 | 4/2014 |
| WO | 2015017721 A1 | 2/2015 |
| WO | 2015138855 A1 | 9/2015 |
| WO | 2016160584 A1 | 10/2016 |

OTHER PUBLICATIONS

Douglass, et al., "Population Genomics Shows No Distinction Between Pathogenic *Candida krusei* and Environmental *Pichia kudriavzevii*: One Species, Four Names", PLoS Pathogens, Jul. 19, 2018 (Jul. 19, 2018), vol. 14, No. 7, pp. 1-27.

Galgoczy, et al., "Checkpoint Adaptation Precedes Spontaneous and Damage-Induced Genomic Instability in Yeast", Molecular and Cellular Biology, Mar. 1, 2001 (Mar. 1, 2001), vol. 21, No. 5, pp. 1710-1718.

Kim, et al., "Metabolic Engineering of a Haploid Strain Derived from a Tripioid Industrial Yeast for Producing Cellulosic Ethanol", Metabolic Engineering, Feb. 16, 2017 (Feb. 16, 2017), vol. 40, pp. 176-185.

Mutoh, et al., "Pro-oxidant Action of Phloxine B on Fission Yeast Schizosaccharomyces pombe", Yeast, Jan. 30, 2005 (Jan. 30, 2005), vol. 22, Iss. 2, pp. 91-97.

Hoffman Charles S et al: "An Ancient Yeast for Young Geneticists: A Primer on the Schizosaccharomyces pombe Model System", Genetics Primer, Jan. 1, 2015, pp. 403-423, XP55798876, Retrieved from the Internet URL:https://www.genetics.org/content/genetics/201/2/403full.pdf.

(Continued)

*Primary Examiner* — Jennifer E Graser

(57) ABSTRACT

Less-than-diploid *I. orientalis* cells are produced. The cells have at least one unpaired chromosome and may be haploid, i.e., are missing one member of each pair of chromosomes that are present in the wild-type strains. The less-than-diploid cells are useful fermentation strains, performing similarly to diploid strains that are otherwise similarly engineered. The less-than-diploid strains can be mated to produce diploids, which themselves are useful fermentation strains. The less-than-diploid strains are also useful as host strains for producing further genetically modified strains that can be less-than-diploid or mated to produce diploids.

15 Claims, 10 Drawing Sheets

Specification includes a Sequence Listing.

(56) References Cited

OTHER PUBLICATIONS

Nobuo Fukuda et al: "Development of growth selection systems to isolate a-type or [alpha]-type of yeast cells spontaneously emerging from MATa/[alpha]", Journal of Biological Engineering, Biomed Central Ltd, Lo, vol. 7, No. 1, Nov. 21, 2013, p. 27, XP021176300, ISSN:1754-1611, 001:10.1186/1754-1611-7-27.
Pavelka et al., in Nature 468(7321):321-5 (2010).
Whittaker S G et al: "Detection of induced mitotic chromosome loss in Saccharomyces cerevisiae-an interlaboratory study", Mutation Research/Genetic Toxicology, Elsevier, Amsterdam, NL, vol. 224, No. 1, Sep. 1, 1989, pp. 31-78, XP023764396, ISSN:0165-1218, 001:10.1016/0165-1218(89)90005-0.

SEQUENCE LISTING

<160> NUMBER OF SEQ ID NOS: 2

<210> SEQ ID NO 1
<211> LENGTH: 2246
<212> TYPE: DNA
<213> ORGANISM: Issatchenkia orientalis

<400> SEQUENCE: 1

| | | | | | |
|---|---|---|---|---|---|
| aaaagtgttt | cctgttgttc | ttcagtattt | aaagcagtga | acaccttttt | tcagctagac | 60 |
| ctctagtttg | tagtatggta | tatagatgtg | gaagccaact | agagtagcta | aaagatgcgg | 120 |
| cctgtagtat | cgcttataaa | aacaactttg | gcattaaaca | agtttgattg | taaagctcat | 180 |
| tctgaaacag | gttagcgcgt | cttcctggta | aacatcatat | ctcactcaaa | ttctacgcct | 240 |
| ctcttacttt | tcttatgttt | catagtgtct | catgtcctta | tactattcat | gataaagcaa | 300 |
| atgttaaagt | attaatgcaa | cacgacgagt | atgttggtaa | atagctatat | tatttattat | 360 |
| tttaatcttc | agatactaac | ctatacactt | tagattactg | gaagtttaca | tacatttaaa | 420 |
| ggatgttttg | agacagttag | ctgaaacgcc | aattgatgaa | gaattaagca | gtactgacct | 480 |
| tttaaaagat | atgcttgtat | gtacctattt | tactcaattc | accacaactc | aaatactaac | 540 |
| tttttgcttt | tgacagaata | tcaaggaaat | attagaatca | ggctctcccc | ttcaaaaaca | 600 |
| aagttgtgaa | cttattcgaa | tgataagaag | gatatcaact | tctatatacg | atatgatttc | 660 |
| tcaacgtagc | acactaaaaa | cgaagtatgg | gctagatctt | aaaagttggg | atctcgacaa | 720 |
| ttcaatgatg | aatacagaag | atacaaactt | aacaaagaat | atggatatac | acaattcttc | 780 |
| ttccattgat | attgacatcg | atgatgaaga | aatatccact | gctttcagag | atgaggggat | 840 |
| tcactcgagc | ttttgcaata | cggatagtaa | tagcattaaa | acaaaagatg | gttcatctag | 900 |
| aaatggtaag | agattaccca | aagagactat | agcagtactc | aacgaatggt | ttaatgataa | 960 |
| tatcgaaaat | cctatgttc | aaaggaaga | tatatcatac | ttgaaagcta | aaactaacct | 1020 |
| tcaagccagc | caaatcaaaa | attgggtttc | caataaaagg | agaaagagga | agggaagtaa | 1080 |
| agtctcccct | agtatagttg | aaattcttaa | ttaactagca | tcaaatatat | acctttatat | 1140 |
| caaaatacaa | gaattagcaa | tttaacgact | cttaggctta | tctacggttg | attttcaaaa | 1200 |
| tttagccgct | tcggtattgc | aaacaaaggc | taggtgatgc | tttactatct | ggtatatgta | 1260 |
| tactgctgtt | tgtttcaaag | caagtgaaga | tagaaggaat | gtttcaaagt | cgtagggcaa | 1320 |
| aacttggcag | ttcaattcaa | taactcccac | tctaatggta | tagctaaaaa | aagaacaaga | 1380 |
| ggtgtgcgaa | aggaaagatg | tctagtaact | caattttta | ggttttagcg | agtgaagtaa | 1440 |
| tgtttcagat | tcaaagttgt | gttttacatt | ctcaatatac | tgaaatattt | gattaatctc | 1500 |
| aggtttagtc | caaagaataa | taaaataaat | aaaacattgt | caggaatcta | gtgatgctgt | 1560 |
| tcttgtgttt | ctttgaattc | tagagatatg | gctagaatgt | ggaacaagtc | atccactctt | 1620 |
| cgtgtgaaga | agcaacgacc | ttccagaatt | tccaaaacaa | ccaccaaagc | aactatattt | 1680 |
| atagccaaac | caactcccag | atatgttatc | ccgttagaag | tggaggagtt | attgagaaaa | 1740 |
| tatatatcta | gaaacaatct | tgatttaagg | accttaagta | atgtcaagaa | aaaaaataag | 1800 |
| aagcataaaa | cagttgttaa | tggttttact | gcattccgaa | catattactc | aaaattcggc | 1860 |
| aaaacatatg | aagatcaaga | aaaccttct | aaagagttag | caaacttatg | gaagcagacc | 1920 |
| ccttctattc | aatcgacctg | gcgtggttat | tcagaagagt | atcgtgcaag | tgcaacggac | 1980 |
| ttgccatttg | tagaatggtt | tgacacatac | aaatcactaa | taaaacctga | accagagaaa | 2040 |
| cgtgattata | ttactcaaac | aacaacaatg | tcccatttaa | cagttgaaga | tgtctatgat | 2100 |

| | | |
|---|---|---|
| aatctaggtt caaattcaat gaactaaaac gtttctttta atcagtgtat atatatatcg | 2160 |
| atatatattt aattgtttct tacttaaatg gaatataaag tgccgattgt cacatctttt | 2220 |
| ttaatgggtg ttaactattc ttcatc | 2246 |

<210> SEQ ID NO 2
<211> LENGTH: 3306
<212> TYPE: DNA
<213> ORGANISM: Issatchenkia orientalis

<400> SEQUENCE: 2

| | | |
|---|---|---|
| tacagtattc aaacctattt tcaaatattt agctaactta cacattagaa agtaatcttt | 60 |
| cagaattact tgcaggctta cctgaacttc tgcgatatac ctcttctaac aataaatcct | 120 |
| tgtctctcga agatttaaat attcaaataa cttttcttat tttatatctt gaaattctat | 180 |
| gtttggaaca caaaaaatat cctcaactct gttttgtttt gacctcagac tcttcatttt | 240 |
| agacctcaca ccagatctct ttctcttttt aggtttgtat actcgaaaca catctttttt | 300 |
| gactgtttca ccttttggct ctctcccatt atatccatcg acagttaatt gagacaaagt | 360 |
| cttctctttt agtttttccg atgcgctgct cgaacgatct ttaagccgtt gagtttgctc | 420 |
| attttcaaaa aatctttctt cctgctccgc tagatacttt acataatgtt caacttccga | 480 |
| acttctactt ttccacaact gtgtagtgtt agtatatgat tcaagaaaaa caaatcatgt | 540 |
| taaccataaa attagcttac tttacccgac tcttctgaaa tatctgtgaa gcccttaatg | 600 |
| gataagtagt tcataagata ctgcttaact aaacttcgat aaattaagaa tatgttccta | 660 |
| ggcttttttg attctttttc tatttctgat cttagtattt tcttatattc tttttcgtcg | 720 |
| tagccgtgtt cttgtttaac tacttgaaca aactctacgg cgccaacgtt ttgtgaaaca | 780 |
| cttcagatc gatttcttgt acttccagaa tctgttagtt tggccatatc tactgaagtt | 840 |
| cttactaaat aagaatgttg acaaccaagg ggcacatttg ttttcaaag tcatgcaata | 900 |
| gataataact gagtgaaaaa aatatttctg acaaaattaa tctaaagtac cttttttgact | 960 |
| ttgaaacaaa gcatgaaaca ttgtcctgtt tcaaaattca tttctatgct cgaaagtatt | 1020 |
| aatttataag aacgcttttt ttcttcaatg ttctgacaac taaatatggc tagttttgaa | 1080 |
| ttatatagaa aaagcaacta atgtatgaa atgtcactcg ggaaagatgt agggacaatt | 1140 |
| attcttccaa tattaacgat atgcagctta actagtgagt tttgcgataa gaatgagaca | 1200 |
| aggaaaccctt taaatatcga attaccgcgt ttagaatcaa tgagtggtat tcccacgaca | 1260 |
| gaaaattcaa acttaagaag attaattgat gactgtcaag attcctttga gaaggaggtg | 1320 |
| ggaattctta tgaacaatga tttaccccctt actttggtag aggacctatt taaaaggtat | 1380 |
| aaagagtttt tgggaaaaaa tacaagctaa tgaataatct cattgatacg ccccgactgc | 1440 |
| ctgaacattt gactttgat gatcactgga tcttggatga cagcttgtca cttgaaaact | 1500 |
| tgaatgatat accaatgtta caaccatacc aactctctga ttttgaaatt acacaagcag | 1560 |
| aaatcactac aacctccgat atattgggag agccattgac catagaatta agtggctcac | 1620 |
| aactatctga acaaaatact ccaatatttt cacaaaattt tggaatttat gattatttga | 1680 |
| attctattac aaatgaaatt gaatcatcaa ctactgatag tgggcacaac cgaagacatc | 1740 |
| gtccatcaaa agatgttaaa gaaaaacttg agcaaatatt tactaaagta aagaaccca | 1800 |
| acagtgtcga gcgtgaatat atagctaaaa agtgtaacat gacgccaacg caagtgagga | 1860 |
| tttggtttac caataaaaga gcaagacaaa taaaaacaag ggatacttag gtcataaaaa | 1920 |

```
-continued accattttg caattgcagt ctattataaa ataagtttta tcgctattta atcataacct    1980
atataccata aatatacatt cactcttcac cgctatcatc atctttataa ctgaactttc    2040
tgatttcacc caatctttt cttgctgaag aaagagcgtt ctccagtttt aaaatttcaa    2100
cttgttgttc catttccgca gtcttatttt catggatgga aagtttgcta taatcgatat    2160
cttcgacttc atgtttacca attatcaatt tattgacttg atcaactagt tgtttacaag    2220
ccaggttgac tttctttgac gcatcttcta gcttgttctg ggtctttgac ataaattggg    2280
attttactct agcggcagaa accaactgag ctgtggatgc tgcaacttct cttgatgcca    2340
caaccaactc ttcatttgaa tgcttattct gtaagactcc gtctgctatt cttatcaaag    2400
tatttgtaga atatgcaatt gacttagacg ccgatattaa accttcggtc cacttattat    2460
ttttcttata aaaggacgtt tttgaatgtg atcctctacc attattgaca atctcttctt    2520
gagattcgat agatgcacga atcaagtatt taatggctgt aatgattgcg gaggcagctg    2580
ccaagatcga cttattaact tcaatgtcaa ttgatgacat tgaaacatca aaaggttgat    2640
tcaaaagtga tgataaatga acagaagctt cctcaataac tctagatgca tgttccattt    2700
ctttatcaac caaatcactc aattcaccgt caactttgct gagatcaatc ttggagctag    2760
gtgtcttcat ggattctact aactgtaata atgtttggag gatctcttga acatcaatat    2820
taccattgat tacaatatca gtttgatcat caatactttt attgacaaga ttcgaatgat    2880
atagggactc caaataaact tcagaaatct cagcaatgtc cttcgcagta tcaattagat    2940
catcttggaa atcatcctgc tttgttaatc tagtcaaacc ttttgtattc agtaaaatat    3000
cgctgattga tgttgtaaaa tttgtaatac tatcaatgac gagagcttca ttggcattat    3060
caccatctac taacatgtta ttaaagcttg aggcaaagtc agtaaccaaa ccagaagatt    3120
tctcaagtaa agttaagaca tattccgggg aagagttcaa attacctgct tgcataggag    3180
aatctaattc aaagacagca tcctgaattc tattaatacc cgattttaaa atagcatcaa    3240
taaggcccag aactttggta gaatttagtt tattctgcat ctcagatttt tcttctctag    3300
aatttt                                                               3306
```

GENETICALLY MODIFIED HAPLOID *ISSATCHENKIA ORIENTALIS*

CROSS-REFERENCE TO RELATED APPLICATIONS

This application is a national phase application of International Application No. PCT/US2018/044998, 2 Aug. 2018, entitled "GENETICALLY MODIFIED HAPLOID *ISSATCHENKIA ORIENTALIS*", which claims the benefit of U.S. Provisional Patent Application No. 62/546,662, filed 17 Aug. 2017, entitled "GENETICALLY MODIFIED HAPLOID *ISSATCHENKIA ORIENTALIS*", each of which are hereby incorporated by reference in their entirety.

*Issatchenkia orientalis* is a diploid yeast that is engineered for industrial-scale fermentations. *Candida krusei* is considered to represent the anamorphic form of *I. orientalis*. *C. krusei* is widely distributed in nature, often occurring in soil, on fruits and in various natural fermentations.

Yeast such as *S. cerevisiae* can undergo meiosis to produce viable haploid cells. Haploid cells that are of opposite mating types can mate to produce new diploid strains. The existence of viable haploid *S. cerevisiae* cells simplifies genetic engineering of that yeast. Genetic material can be inserted at the identical locus in each of the haploid cells. When the cells are mated to form a diploid strain, the inserted material will be present on both copies of the affected chromosome. The resulting diploid strain is usually stable with respect to the inserted genetic material.

The ability to engineer haploids and mate them to produce stable strains greatly simplifies and speeds genetic engineering. Engineering diploid strains requires insertion at the same locus in each member of a chromosomal pair, if a stable strain is to be produced. This must be done sequentially, usually with additional engineering steps to recycle selection markers. Engineering steps and time are saved by engineering the haploids separately and mating them.

Haploid *Issatchenkia orientalis* has not been identified in nature. This yeast is not known to have a sexual cycle that produces viable haploid spores. Therefore, the genetic engineering of *I. orientalis* has been slow and laborious due to the need to separately insert exogenous genes into each copy of a chromosome pair in the diploid strain. A more efficient way of engineering *I. orientalis* would be very desirable.

This invention is in one aspect a viable *Issatchenkia orientalis* that is less-than-diploid.

The viable less-than-diploid *Issatchenkia orientalis* strain has been found to be a useful fermentation strain, in some cases performing comparably to diploid *I. orientalis*. This is entirely unexpected due to the lack of naturally occurring haploid *I. orientalis* in nature. The strain is also useful for making genetically modified diploid *I. orientalis*. Genetic modifications are made easily and rapidly in the less-than-diploid strains. By mating the less-than-diploid strains with differing genetic modifications, daughter diploid cells having diverse genotypes can be produced rapidly and easily.

The invention is also a method of making a *I. orientalis* organism that is less-than-diploid, comprising the steps of:
a) growing parent diploid and/or tetraploid *I. orientalis* cells in the presence of an agent that binds to microtubules, disrupts microtubule formation and/or enhances microtubule depolymerization such that at least some of the diploid and/or tetraploid cells divide to form viable daughter cells that are less-than-diploid; and then
b) identifying at least a portion of the viable daughter cells that are less-than-diploid.

The invention is also a method of identifying viable *I. orientalis* cells that are less-than-diploid, comprising:
a) forming isolates of viable *I. orientalis* cells that include putative less-than-diploid cells;
b) separately growing the isolates in the presence of a dye that differentially stains *I. orientalis* cells having less-than-diploid DNA content and *I. orientalis* cells having at-least-diploid DNA content, to form *I. orientalis* colonies; and
c) identifying less-than-diploid *I. orientalis* colonies on the basis of a difference in visual appearance from diploid *I. orientalis* colonies due to the differential staining.

The invention is also a method of producing a genetically modified *I. orientalis* that is at-least-diploid comprising:
a) mating
1) a first less-than-diploid *I. orientalis* strain that contains only one copy of a chromosome that contains a mating factor gene, wherein the mating factor gene encodes for an α-mating factor; with
2) a second less-than-diploid *I. orientalis* strain that contains only one copy of a chromosome that contains a mating factor gene, wherein the mating factor gene encodes for an a-mating factor;
to produce an *I. orientalis* strain that is at-least-diploid and
b) isolating said at-least-diploid *I. orientalis* strain.

Figure 1A:
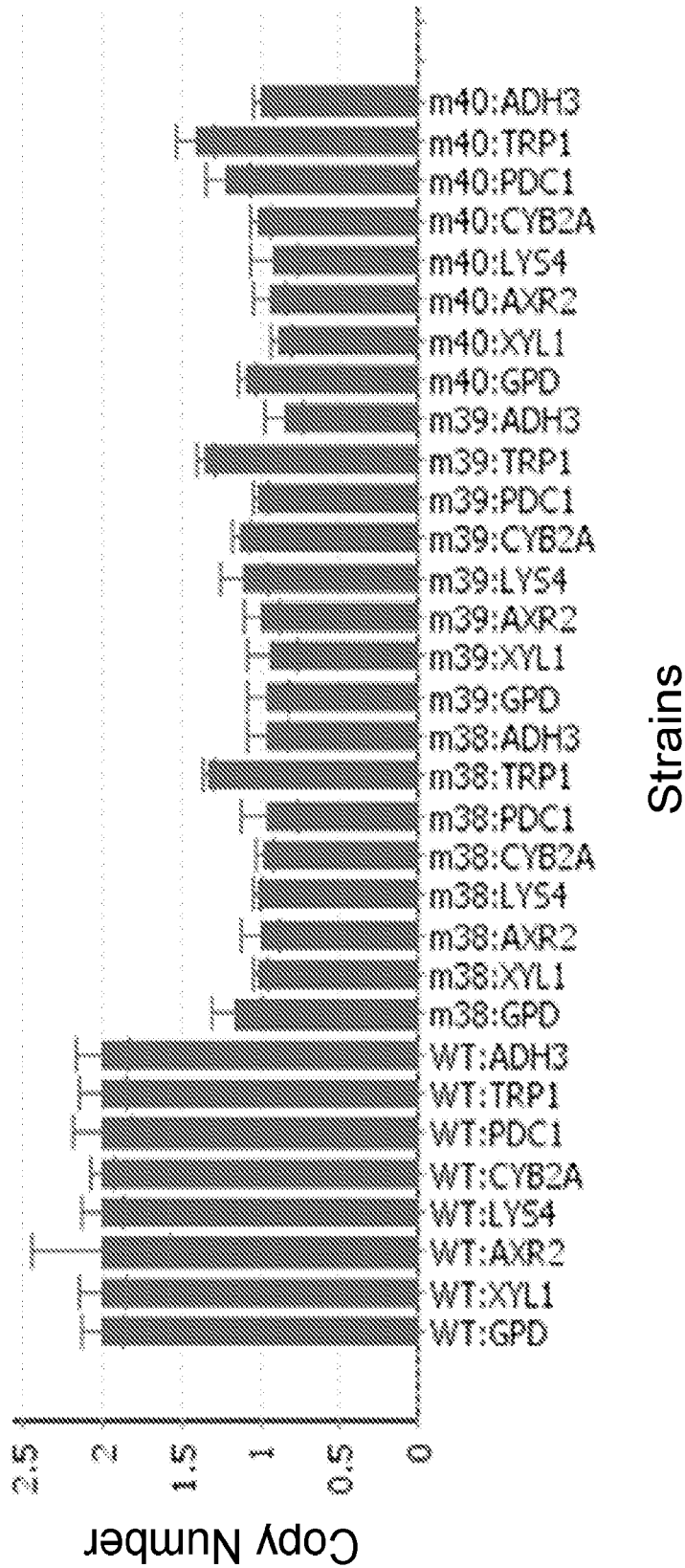
FIG. 1A is a graph showing the copy number at various loci for a control diploid strain and three less-than-diploid strains.

By "less-than-diploid", it is meant that, the modified *I. orientalis* has only a single copy of at least one chromosome during the resting phase ($G_0$) and Gap 1 growth phase ($G_1$) of its cell cycle, i.e., that at least one member of at least one pair of chromosomes present in wild-type *I. orientalis* is absent from the modified *I. orientalis* organism. A diploid *I. orientalis* cell has paired copies of all its chromosomes during the $G_0$ and $G_1$ phases of its cell cycle. The resting phase $G_0$ refers to a stage in which the cell is not engaged in mitotic reproduction. The $G_1$ growth phase is the period in which the cells grow prior to entering mitosis. The $G_1$ growth phase precedes the DNA synthesis phase (S) of the mitotic cycle in which the chromosomes are duplicated in preparation for cell division.

By "viable", it is meant the organism grows, i.e., it engages in mitotic reproduction when cultured to produce new cells. In general, viability requires the presence of at least one member of each pair of chromosomes present in the wild-type strain. Thus, a modified *I. orientalis* organism of this invention has a number of chromosomes ranging from N to 2N−1, where 2N is the number of chromosomes present in wild-type *I. orientalis*, provided further that it possesses at least one member of each chromosome pair present in wild-type *I. orientalis*. In some embodiments, the modified *I. orientalis* of the invention contains N to N+2 chromosomes, again provided it possesses at least one member of each chromosome pair present in wild-type *I. orientalis*. In some embodiments, the modified *I. orientalis* organism of the invention is haploid, i.e., contains one and only one member of each pair of chromosomes present in the wild-type strain, the total number of chromosomes being exactly N.

A chromosome is "paired" in cases in which both members of a chromosome pair are present in a strain under consideration during the $G_0$ and $G_1$ phases of its growth cycle. An "unpaired" chromosome is one of which there is only one copy in a strain under consideration during the $G_0$ and $G_1$ phases of its growth cycle; i.e., one member of the chromosome pair present in a diploid *I. orientalis* strain is missing at such times.

In some embodiments, the viable *Issatchenkia orientalis* cell contains only one copy of a chromosome that contains a mating factor gene. The mating factor gene may be one or more α-mating factor genes, in which case the chromosome carrying a-mating factor gene(s) is absent from the strain. Alternatively, the mating factor gene may be an a-mating factor gene in which case the chromosome carrying the α-mating factor gene(s) is absent from the strain. Wild-type *I. orientalis* contains two copies of the α-mating factor genes on one member of a chromosome pair and two copies of the a-mating factor genes on the other member of the pair.

The less-than-diploid *I. orientalis* organism of the invention is produced in a method that includes a step of growing parent diploid and/or tetraploid *I. orientalis* cells in the presence of an agent that binds to microtubules, disrupts microtubule formation and/or enhances microtubule depolymerization. The agent may be, for example, one or more of nocodazole, benomyl, colchicine, or para-fluoro-phenylalanine. Benomyl is a preferred agent because it tends not to greatly inhibit cell division. The amount of such agent may be, for example, 10 to 10,000 μg per mL of culture, with a preferred amount being 25 to 250 μ/mL. Cells are grown up in a culture medium that contains the agent as well as a carbon source and nutrients as may be required by the strain to grow and divide to form daughter cells. The culture medium may be, for example a yeast extract or other medium that contains a carbon source and other nutrients needed for the cells to grow. Growth conditions are in general not critical. Culturing temperature may be, for example, 20 to 40° C.

Although the invention is not limited to any theory, it is believed that the presence of the agent disrupts the usual allocation of a complete diploid set of chromosomes to each daughter cell during mitosis. The chromosomes are instead distributed erratically to the daughter cells, so that at least some of the daughter cells receive fewer than a full complement of chromosomes and are less-than-diploid. The erratic distribution of chromosomes may result in a population of cells that do not contain at least one member of each chromosome pair. These are not viable and will die off. A population of cells having N to 2N−1 chromosomes in which at least one member of each chromosome pair is present will also form. These are viable, less-than-diploid cells of the invention.

At least a portion of the viable, less-than-diploid cells is identified. There are various ways of isolating these cells, including, for example, differential staining, fluorescence-activated cell sorting (FACS); identifying daughter cells that have are not heterozygous at a locus at which the parent cells are heterozygous; quantitative PCR (qPCR) methods such as are described, for example, by Pavelka et al., in *Nature* 468(7321):321-5 (2010), entire genome sequencing and read depth analysis methods, and by growth in particular selective medium. These methods can be used singly or in various combinations. The presence of only a single member of a chromosome pair can be determined by performing a single deletion of a gene that resides on each member of such chromosome pair and evaluating the cell for the presence of the function of a gene product encoded by the deleted gene. The absence of the function indicates the presence of only a single member of the chromosome pair, whereas the presence of both members of the pair is indicated when the function is retained despite the single deletion.

In the differential staining method, daughter cells are streaked for isolates and grown in the presence of a dye to form colonies. The dye is one that differentially stains *I. orientalis* cells having less-than-diploid DNA content and *I. orientalis* cells having at-least-diploid DNA content.

An example of such a dye is Phloxine B, which has the physical form of a red to brown powder and the chemical formula $C_{20}H_2Br_4CL_4Na_2O_5$. Phloxine B stains *I. orientalis* cells pink or red. It has been found that the diploid or greater than diploid (such as tetraploid) cells stain darker with this dye than do less-than-diploid cells. Therefore, less-than-diploid cells are identified by comparing their appearance to that of similarly stained diploid *I. orientalis* colonies. Colonies of less-than-diploid cells are a lighter pink color than the colonies of diploid *I. orientalis*. The less-than-diploid colonies may be white or nearly white in appearance, even when grown in the presence of the stain.

To identify cells using fluorescence-activated cell sorting (FACS), daughter cells are stained with a fluorescent tag. A fluorescent tag that intercalates or otherwise binds to DNA such as ethidium bromide or Sytox™ Green (available from Thermofisher) is suitable. Sytox™ Green has the chemical structure:

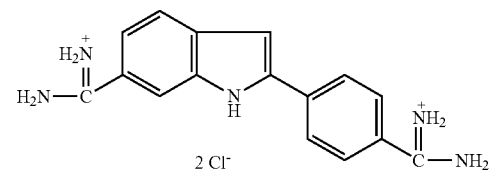 [SMILES: N=C(N)c1ccc(-c2cc3ccc(C(=N)N)cc3[nH]2)cc1]

The stained daughter cells are passed through a flow cytometer such as a BD Accuri C6 flow cytometer from BD Biosciences or equivalent), where the fluorescent tag is excited by exposure to electromagnetic energy at a wavelength that is absorbed by the fluorescent tag and causes it to fluoresce. The wavelength of the exciting radiation is selected in conjunction with the particular fluorescent tag in known manner. The stained cells fluoresce at a lower wavelength that is characteristic of the particular fluorescent tag. The intensity of the fluorescence is measured and compared to the intensity of fluorescence of a known diploid. The flow cytometer can be programmed to deflect cells exhibiting a fluorescence intensity within a specific range associated with less-than-diploid cells to separate those cells from diploid or other cells, thereby isolating the less-than-diploid cells.

Figure 2:
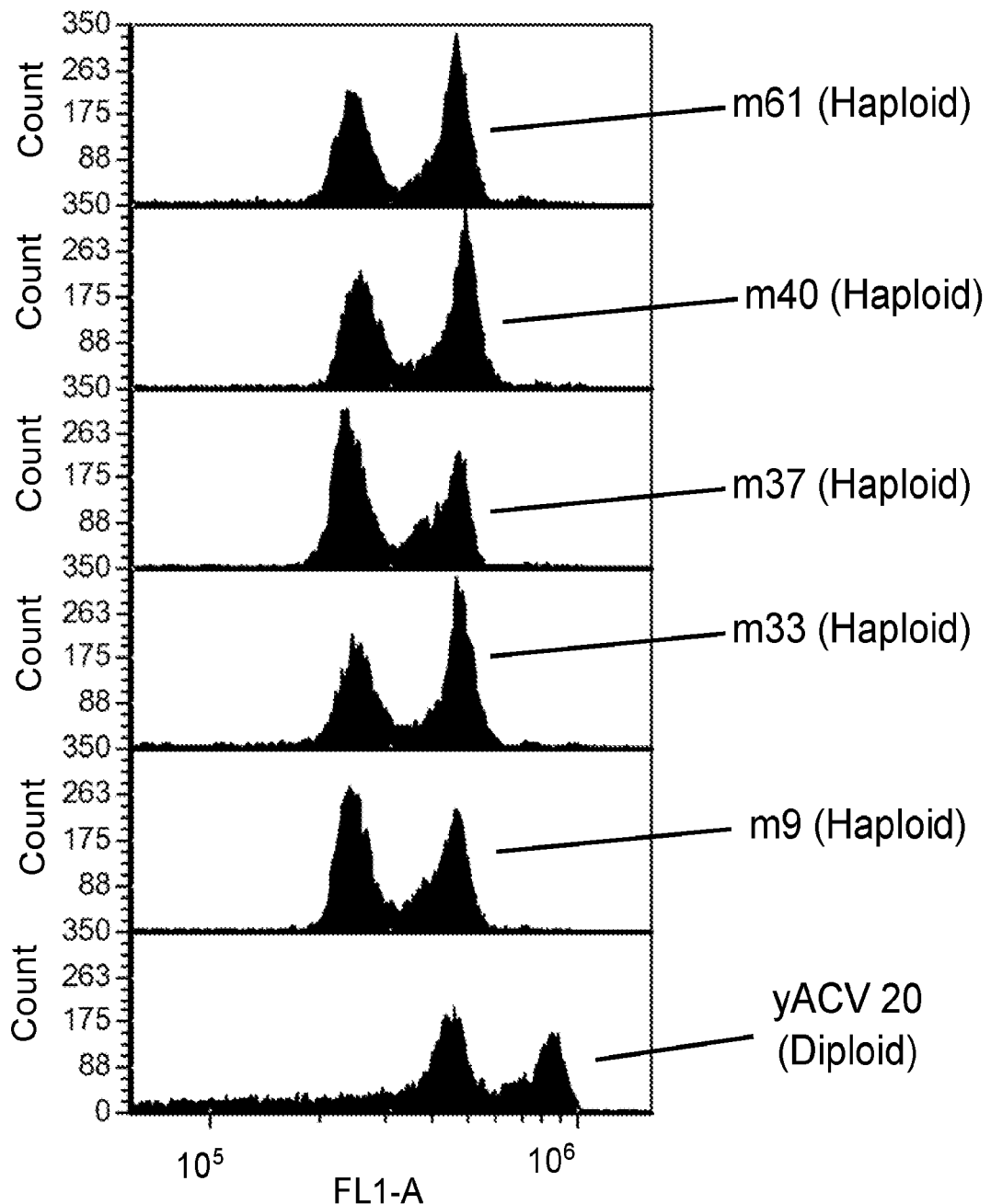
FIG. 2 is a histogram showing fluorescent intensity as measured by fluorescence-assisted cell sorting for a known diploid strain and a less-than-diploid strain of the invention.

It is convenient to grow one or more colonies of a known diploid *I. orientalis* strain, stain the cells, and pass cells from such a colony through the flow cytometer. The fluorescence intensity of each cell is measured, and a histogram is produced that plots the number of events versus intensity. Because a growing colony will contain cells that are undergoing mitosis, the histogram produced from such a colony typically produces two major peaks, one corresponding to a population of cells which are undergoing mitosis and one corresponding to a population of cells that are in the $G_0$ or $G_1$ phases of the cell cycle, as shown in FIG. 2. The median fluorescence intensity of each of the major peaks is determined using appropriate software. The median of the lower intensity peak is taken as the fluorescence intensity of the known diploid strain.

Cells from a colony of a putative less-than-diploid strain are similarly stained and passed through the flow cytometer to produce a histogram in the same manner. Again, the median of the lower intensity peak so produced is taken as the fluorescence intensity of the putative less-than-diploid strain.

The median value of the lower intensity peak has been found to be approximately proportional to the amount of DNA in the cells, and therefore indicative of the number of chromosomes that are present. An *I. orientalis* strain that exhibits a fluorescence intensity at least 20% lower than that of the known diploid strain is considered for purposes of this invention to be less-than-diploid, as such a fluorescence intensity indicates a loss of approximately 20% of its DNA, which is enough to indicate the loss of at least one chromosome relative to the known diploid strain. An *I. orientalis* strain that exhibits a fluorescence intensity of 40 to 60%, especially 45 to 58% or 50 to 57%, of that of the known diploid strain is a likely haploid strain.

Less-than-diploid daughter cells can also be identified on the basis of a loss of heterozygosity. "Heterozygous" and its various grammatical forms mean that one member of a chromosome pair of the parent diploid or tetraploid *I. orientalis* has a different nucleotide sequence at a specific locus than does the other member of the pair.

The difference may be as small as one base pair or as large as a gene or more. The difference may be a deletion (missing nucleotide or nucleotides), insertion (one or more added nucleotides) or substitution (replacement of one or more nucleotides with one or more different nucleotides).

The difference in nucleotide sequence may be naturally-occurring. For example, single nuclear polymorphisms (SNPs, i.e., differences in a single nucleotide at a specific locus) commonly occur between members of chromosome pairs, and can be identified by sequencing methods. In some cases, the alleles of one or more genes are different between the members of a chromosome pair; an example of this is the α mating factor and a-mating factor genes of *I. orientalis*.

Heterozygosity can be produced by engineering the strain to delete, insert or substitute one or more nucleotides from one member of a chromosome pair but not the other. This may include, for example, the insertion of a gene into only one member of the chromosome pair and/or deletion of a gene from only one member of the chromosome pair.

Loss of heterozygosity can be determined, for example, by sequencing methods and PCR methods. Using PCR, primers are designed to isolate heterozygous loci such as an SNP from each member of a chromosome pair. Upon subsequent PCR, the presence of only one band, which corresponds to only one of the heterozygous loci, indicates that the heterozygosity has been lost in that cell and that a member of the chromosome pair carrying that heterozygous site has been lost.

In some embodiments, the heterozygosity involves a deletion or disruption of a native gene from only one member of a chromosome pair. The deletion of that native gene causes the cell to be resistant to a selection agent. Daughter cells that contain the chromosome with the deleted or disrupted gene but not the other member of the pair will be resistant to such selection agent, whereas the parent strains will not be. Growth in the presence of such a selection agent therefore provides a means for identifying daughter cells that have lost the chromosome carrying the native gene. The native gene that when deleted or disrupted confers resistance to a selection agent may be, for example, a orotidine-5'-phosphate decarboxylase (URA3) gene, in which case the selection agent is 5-fluroorotic acid. The deleted or disrupted native gene may be a tryptophan synthase (TRP1) gene, in which case the selection agent is 5-fluroanthranilic acid. The deleted or disrupted native gene may be an arginine permease gene in which case the selection agent is canavanine. The deleted or disrupted native gene may be a yeast ribosomal protein (CYH2) gene in which case the selection agent is cycloheximide.

The less-than-diploid *I. orientalis* cell of the invention may have modifications to one or more of its remaining chromosomes.

In some embodiments, the cell of the invention contains an insertion of one or more exogenous base pairs onto one or more of its chromosomes. By "exogenous", it is meant that the inserted base pair(s) are not present in the wild type *I. orientalis* at the locus at which the inserted base pair(s) are present. The inserted base pairs in some embodiments may include (i) a gene that is not native to wild-type *I. orientalis*, (ii) a gene which is native to *I. orientalis* but is present at a different locus in the wild-type *I. orientalis* strain and/or (iii) one or more additional copies of a gene which is native to wild-type *I. orientalis*. In each case, the gene preferably encodes for a gene product in the modified *I. orientalis* strain. A "gene product" includes, for example, RNA and a polypeptide (including an enzyme) encoded by the gene.

The exogenous gene may be, for example, a selection marker gene. A "selection marker gene" is one that encodes a protein needed for the survival and/or growth of the transformed cell in a selective culture medium. Typical selection marker genes encode proteins that (a) confer resistance to antibiotics or other toxins (e.g., resistance to bleomycin or zeomycin (e.g., *Streptoalloteichus hindustanus* ble gene), aminoglycosides such as G418 or kanamycin (e.g., kanamycin resistance gene from transposon Tn903), or hygromycin (e.g., aminoglycoside antibiotic resistance gene from *E. coli*) (b) complement auxotrophic deficiencies of the cell (e.g., deficiencies in leucine (e.g., the LEU2 gene), uracil (e.g., the URA3 gene), or tryptophan (e.g., the TRP gene)), (c) enable the cell to synthesize nutrients not available from simple media, or (d) confer the ability for the cell to grow on a particular carbon source. Exemplary selection markers include the URA3 gene, zeocin resistance gene, G418 resistance gone, and hygromycin resistance gene. A selection marker gene is operatively linked to one or more promoter and/or terminator sequences that are operable in the host cell. In certain embodiments, these promoter and/or terminator sequences are exogenous promoter and/or terminator sequences that are included in the selection marker cassette.

The exogenous gene may confer upon the cell the ability to produce a metabolic product that is not produced by the wild-type cell, an enhanced ability to a metabolic product produced by the wild-type cell, and/or an alternative metabolic pathway to produce a metabolic product produced by the wild-type cell.

Because *I. orientalis* has excellent resistance to low pH and the presence of organic acids, the exogenous gene may include one or more genes that encode for polypeptides that catalyze one or more metabolic steps in the synthesis of organic acids including, for example, a hydroxyl acid such as lactic acid or 3-hydroxypropionic acid, an, a fatty acid such as a $C_4$-$C_{12}$ fatty acid, a dicarboxylic acid such as succinic acid, fumaric acid or maleic acid, a tricarboxylic acid such as citric acid and the like.

The exogenous gene may be, for example, a lactate dehydrogenase (LDH) gene, which confers upon the cell the ability to produce lactate. Examples of useful LDH genes include L-lactate dehydrogenase (L-LDH) genes and D-LDH genes as described on page 5 of WO 2007/032792, incorporated herein by reference.

The exogenous gene may include one or more genes that enable the cell to produce succinate and/or one or more metabolic products that the cell can further metabolize to succinate. Such genes may include one or more of i) an exogenous pyruvate carboxylase gene that encodes for an enzyme which catalyzes the conversion of pyruvate to oxaloacetate, (ii) an exogenous malate dehydrogenase gene which encodes for an enzyme that catalyzes the conversion of oxaloacetate to malate, (iii) an exogenous fumarase gene that encodes for an enzyme which catalyzes the conversion of malate to fumarate and (iv) an exogenous fumarate reductase gene that encodes an enzyme which catalyzes the conversion of fumarate to succinate. Such genes are described, for example, in WO 2014/018757, the relevant portions thereof are incorporated by reference herein.

The exogenous gene may include one or more genes that enable the cell to produce fatty acids and/or one or more metabolic products that the cell can further metabolize to a fatty acid. The exogenous gene may include one or more 3-ketoacyl-CoA synthase, 3-ketoacyl-CoA reductase, 3-hydroxyacyl-CoA dehydrase and trans-2-enol-CoA reductase genes such as are described in WO 2014/051135 and U.S. Provisional Application No. 62/453,817, both incorporated by reference herein. These genes together provide a metabolic pathway for the synthesis of fatty acids, in particular fatty acids having 4 to 12 carbon atoms, as described in the foregoing references.

The exogenous gene may include one or genes that enable the cell to produce 1-butanol and/or one or more metabolic products that the cell can further metabolize to 1-butanol. Such genes may include one or more of: i) a pyruvate-formate lyase gene, ii) a pyruvate dehydrogenase gene, iii) an acetyl-CoA acetyltransferase gene; iv) a 3-hydroxybutyryl-CoA dehydrogenase gene; v) a 3-hydroxybutyryl-CoA dehydratase gene; vi) a butyryl-CoA dehydrogenase gene; vii) a trans-2-enyl-CoA reductase gene, viii) a acetaldehyde dehydrogenase and ix) a 1-butanol dehydrogenase gene, as described, for example in WO 2008/121701, incorporated herein by reference.

The exogenous gene may include one or genes that enable the cell to produce isobutanol and/or one or more metabolic products that the cell can further metabolize to isobutanol. In some embodiment the exogenous gene is an NADH-dependent ketol-acid reductoisomerase. The cell in some embodiments may have a metabolic pathway that includes the steps of (a) converting pyruvate to acetolactate; (b) converting acetolactate to 2,3-dihydroxyisovalerate; (c) converting 2,3-dihydroxyisovalerate to α-ketoisovalerate; (d) converting α-ketoisovalerate to isobutyraldehyde; and (e) converting isobutyraldehyde to isobutanol, as described, for example in U.S. Pat. Nos. 8,097,440 and 8,232,089. Such a cell may be (i) engineered to reduce or eliminate the expression or activity of an endogenous aldehyde dehydrogenase that catalyzes the conversion of isobutyraldehyde to isobutyrate; and/or (ii) engineered to reduce or eliminate the expression or activity of an endogenous pyruvate decarboxylase that catalyzes the conversion of pyruvate to acetaldehyde, as described in U.S. Pat. No. 8,158,404.

The exogenous gene may include one or genes that enable the cell to produce 3-hydroxypropionic acid and/or one or more metabolic products that the cell can further metabolize to 3-hydroxypropionic acid. Such an exogenous gene may include an exogenous glycerol dehydratase genes such as the *Klebsiella pneumonia* dhaB gene as described in U.S. Pat. No. 6,852,517. The exogenous gene may include an aspartate 1-decarboxylase as described in WO 2015/017721.

The exogenous gene may include one or more genes that encode for polypeptides that help the cell maintain a redox balance. An example of such a gene is an NAD(P)+transhydrogenase gene as described, for example, in WO 2014/018757, incorporated herein by reference.

The exogenous gene may include one or more genes that encode for one or more polypeptides that enable the cell to metabolize certain substrates that the wild-type cell metabolizes poorly if at all. For example, the exogenous gene may include an exogenous xylose isomerase gene and/or an exogenous xylulokinase as described, for example, in WO 2004-000381, incorporated herein by reference.

An exogenous gene may be integrated into one or more unpaired chromosomes of the less-than-diploid strain.

The *Issatchenkia orientalis* cell of the invention may have a deletion or disruption of one or more native genes carried by one or more of the remaining chromosomes of the less-than-diploid cell. A deletion or disruption of one or more genes may include, for example i) the complete removal of the open reading frame of a gene; ii) a removal of one or more base pairs from the open reading frame of a gene such that the gene no longer encodes for a functional gene product; iii) an insertion of one or more base pairs into the open reading frame of a gene such that the gene no longer encodes for a functional gene product; iv) a partial or complete removal of a promoter and/or terminator of a gene or v) an insertion of one or more base pairs into the promoter and/or terminator of a gene such that the gene is not transcribed by the cell.

In some embodiments, the less-than-diploid *I. orientalis* cells includes a deletion or disruption of native gene that when deleted or disrupted confers resistance to a selection agent. Preferably, all copies of such native gene are deleted or disrupted in such less-than-diploid strain. Examples of such native genes include a native orotidine-5'-phosphate decarboxylase gene; a native tryptophan synthase gene, a native arginine permease gene and a native yeast ribosomal protein (CYH2) gene. The absence of such genes permits the less-than-diploid cells to be selected for by their ability to grow in the presence of specific selection agents, as discussed more fully below.

Other genes that may be deleted or disrupted include, for example, a native pyruvate decarboxylase gene as described, for example, in WO 2007/032792; a native xylose dehydrogenase or a native xylose reductase as described, for example, in WO 2004/099381; a native L- or D-lactate: ferricytochrome c oxidoreductase gene as described, for example in WO2007/117282; a native glycerol-3-phosphate dehydrogenase and/or native glycerol-3-phosphatase gene as described in WO 2007/106524; a phosphoribosylaminoimidazole carboxylase (ADE2) gene, a phosphoribosylaminoimidazole-succinocarboxamide synthase (ADE1 gene), an O-acetylhomoserine O-acetylserine sulphydrylase gene (MET15), a L-lactate:cytochrome c oxidoreductase (CYB2) gene, a L-aminoadipate-semialdehyde dehydrogenase (LYS2) gene, and/or a homoaconitate hydratase (LYS4) gene.

Exogenous genetic material and deletions and/or disruptions can be produced in the less-than-diploid strains by a) performing the insertions and/or deletions/disruptions on the less-than-diploid strain itself and/or by b) performing the insertions and/or deletions/disruptions in the parent diploid strain. In case b), an insertion and/or deletion/disruption can be performed on each member of a chromosome pair so that all viable less-than-diploid strains produced therefrom retain that insertion and/or deletion/disruption. Alternatively, the modification can be made on only one member of a chromosome pair of the parent diploid strain, and less-than-diploid strains in which that member is retained but the other member of the chromosome pair has been lost can be selected for.

Methods for inserting exogenous genes into yeast and deleting or disrupting yeast genes are well known in the art and are described in, for example, WO99/14335, WO00/71738, WO02/42471, WO03/102201, WO03/102152, WO03/049525, WO07/032792, WO2008/121701, WO 2014/018757 and WO 2014/051135. Such methods are generally applicable to making genetic modifications to *Issatchenkia orientalis* diploids and less-than-diploids.

The less-than-diploid yeast of the invention is, depending on its particular genetic modifications, useful for fermenting a fermentable carbohydrate to one or more fermentation products. Generally, this is done by culturing the less-than-diploid yeast in a medium that includes at least one carbohydrate that is fermentable by the yeast; nutrients as required by the particular cell, including a source of nitrogen (such as amino acids, proteins, inorganic nitrogen sources such as ammonia or ammonium salts, and the like), and various vitamins, minerals and the like. The medium may be a defined medium or a complex medium such as yeast extract. Methods for culturing yeast to make various fermentation products as described, for example, in WO99/14335, WO00/71738, WO02/42471, WO03/102201, WO03/102152, WO03/049525, WO2008/121701, WO 2014/018757 and WO 2014/051135, are suitable.

The fermentation product may be any that is produced naturally by wild-type *I. orientalis* and/or one that the modified *I. orientalis* of the invention has been modified to produce by the integration of a suitable metabolic pathway and/or elimination of one or more native metabolic pathways.

Thus, for example, the fermentation product may be a carboxylic acid compound such as a hydroxy acid, an amino acid, a fatty acid, a dicarboxylic acid and/or a tricarboxylic acid. Such a hydroxy acid may be, for example, glycolic acid, lactic acid, 3-hydroxyproprionic acid and the like. The fatty acid may be, for example, a $C_4$ to $C_{12}$ fatty acid. The diacid may be, for example, succinic acid, fumaric acid or maleic acid. The triacid may be, for example, citric acid. Any of the acids may be produced in the form of the free acid, a salt thereof and/or an ester thereof.

The fermentation product may be an alcohol compound such as ethanol, 1-propanol, isopropanol, 1-butanol, isobutanol, glycerol and the like.

The less-than-diploid cell of the invention is also useful for making genetically modified diploid (or greater-than-diploid) *I. orientalis* cells. A disadvantage of engineering diploid *I. orientalis* is that parallel modifications must be made to each member of a pair of chromosomes to produce a stable strains. This is cumbersome because the parallel modifications generally need to be made sequentially, so multiple genetic engineering steps are needed. Furthermore, it is usually necessary to recycle selection markers so they can be re-used in the successive transformations. This adds even more genetic engineering steps.

The less-than-diploid strain of the invention allows for simpler engineering because the transformations need to be made only once to each member of a mating pair, if the less-than-diploid strain contains only one copy of the chromosome or chromosomes at which modifications are made.

In some embodiments of the invention, less-than-diploid strains of the invention can be mated to produce at-least-diploid progeny that contain the chromosomes of both of the mated less-than-diploid strains. In such embodiments, a less-than-diploid strain is produced which has only one copy of the chromosome bearing a mating factor, and only one mating factor gene (the α mating factor (MATα) gene or the a mating factor (MATa) gene). A second less-than-diploid strain is produced which has only one copy of the chromosome bearing a mating factor gene, and only the opposite mating factor gene. It has been found that such less-than-diploid *I. orientalis* cells will mate, despite the lack of haploid mating amongst *I. orientalis* in nature. Mating is achieved by mixing the less-than-diploid strains with the opposite mating factors as just described and growing them. Mating occurs spontaneously under growth conditions. The at-least-diploid strains produced by mating can be identified and isolated using techniques as described before for distinguishing diploid from less-than-diploid strains.

The at-least diploid strain so produced typically will be at-least-diploid and contains at least two copies of each chromosome. The at-least-diploid strain may contain a number of chromosomes equal to the combined number of chromosomes processed by the mated less-than-haploid strains. It may contain more than two copies of one or more chromosomes. It may contain exactly two copies of each chromosome.

The ability of the less-than-diploid cells with opposite mating factors to mate further increases the value of the less-than-diploid cells as genetic engineering strains. Stable at-least-diploid strains are easily made by making the same genetic modifications to each of a pair of less-than-diploid strains that have opposite mating types (provided that the modification are made to a chromosome that is present in only one copy each of the less-than-diploid strains), and then mating the modified less-than-diploid strains. Thus, a gene that encodes a gene product may be integrated into each of the starting less-than-diploid starting strains, in each case at a locus of a chromosome that is present in only one copy. The transformed strains are then mated to produce an at-least-diploid strain in which the gene is present on both members of the chromosome pair. This process speeds genetic engineering of *I. orientalis* strains because the modifications to each less-than-diploid strain can be done simultaneously rather than sequentially, and no steps of recycling markers are needed.

The ability to mate less-than-diploid cells of the invention to produce at-least-diploids is additionally valuable because strains having genetic diversity can be produced easily and rapidly. A cell of one less-than-diploid cell can be engineered with a first set of genetic modifications, which will typically include the insertion of one or more exogenous genes that encode for gene products. A cell of a different less-than-haploid cell with opposite mating factor can be engineered with a second set of genetic modifications, again typically including the insertion of one or more genes that encode for gene products. Such modifications in each case are preferably performed on chromosomes that are present in only one copy in the less-than-diploid cells. Upon mating, at-least-diploid cells are produced that have the modifications (including the exogenous genes) of both strains. This allows, for example, for the rapid and easy production of strains for use in evaluating the performance of specific exogenous genes in the yeast strain, or for evaluating how combinations of exogenous genes perform in the strain.

The invention will be further described by the following non-limiting examples. All parts and percentages are by weight unless otherwise indicated.

EXAMPLE 1

A diploid *I. orientalis* strain is engineered to place a native sequence (SEQ. ID. NO. 1) that contains two a-mating factor (MATa) alleles and an intervening sequence with a sequence native to the other member of that chromosome pair (SEQ. ID. NO. 2) that contains two α mating factor (MATα) alleles and an intervening sequence. The strain is further engineered to, delete one of the alleles of the TRP1 gene, and to delete both alleles of the orotidine-5'-phosphate decarboxylase (URA3) gene. This strain is then is transformed with a DNA fragment (containing the URA3 gene as a selectable marker) to delete one of the native midazoleglycerol-phosphate dehydratase (HIS3) alleles. This diploid strain is further transformed with a PCR product to delete only one of the arginine permease (CAN1) genes, using the native hygromycin-B 4-O-kinase (hph) gene as a selectable marker. The URA3 gene at the HIS3 locus is then looped out by selection on media containing 5-fluoroorotic acid.

The resultant diploid strain is designated yACV20. yACV20 has two MATα alleles on each of member of the relevant chromosome pair, but no MATa allele (MATα/MATα genotype); a double deletion of the ura3 alleles (ura3Δ/ura3 Δ genotype), a deletion of one of the TRP1 alleles (TRP1/trp1 Δ genotype), a deletion of one of the HIS3 alleles (HIS3/his3 Δ genotype) and a deletion of one of the CAN1 alleles (CAN1/can1 Δ genotype).

Strain yACV20 cells are inoculated into 12 mL of YPD and separated into 4 tubes. Benomyl is added to three of the tubes at concentrations of 50 µg/Ml, 100 µg/mL and 200 µg/mL, respectively. No benomyl is added to the fourth tube. The strains are grown at room temperature for 20 hours. Growth is seen in all four tubes, although growth rates are lower with increasing concentrations of benomyl.

The strains from the tubes containing 50 µg/mL and 100 µg/mL benomyl are washed with water, diluted, plated onto SD plates that lacks arginine and contains canavanine and incubated for 2 days at room temperature. Colonies are picked to a fresh plate and incubated overnight. Growth on these canavanine plates indicates that the treated strains have lost the chromosome containing the CAN1 gene. Strains that retain a copy of the CAN1 gene (including the parent diploid strains) are unable to grow on this medium.

Cells that grow on the canavanine medium are grown on a YPD+phloxine B plate. The resulting colonies exhibit a white to very light pink color and are distinguishable from known diploid *I. orientalis* cells (which stain darker pink) on this basis.

The red and light-pink colonies are then tested for loss of chromosomes using by SNP (single nuclear polymorphism) assay. Cells from the phloxine B plate are lysed in Y-Lysis buffer (Zymoresearch) and treated with 2 µl of zymolyase (Zymoresearch) to obtain genomic DNA. The DNA is then used in a PCR reaction to determine the presence or absence of known SNPs at select loci (within the NADH-preferring xylose reductase (XYL1) locus, the aldose reductase (AR2) locus, the homoaconitate hydratase (LYS4) locus, the L-lactate:cytochrome c oxidoreductase (CYB2A) locus, the pyruvate decarboxylase (PDC1) locus, the tryptophan synthase (TRP1) locus and the aldehyde dehydrogenase (ADH3) locus)) in the genome. The presence of the SNPs at a locus indicates that the yeast retains both copies of the chromosome carrying that locus, but the absence of a SNP indicates a loss of one chromosomes carrying that locus.

The red colonies on Phloxine B are found to have retained most or all of the SNPs, while the light pink colonies have lost two or more of the SNPs, indicating that the light pink colonies are less-than-diploid.

Cells from colonies that show light coloration when stained with phloxine B and which have lost 2 or more SNPs are designated as m9, m33, m37, m38, m 39, m40, m41, m42, m43, m60, m61, m62.

Isolates m33, m37, m38, m 39, m40, m41, m42, m43, m60, m61, m62 are taken for analysis by quantitative PCR (qPCR), using methods as described generally by Pavelka et al., in *Nature*, 2010 Nov. 11; 468(7321):321-5. For the qPCR assay, genomic DNA is obtained from the strains by first normalizing the concentration of the cells to the same $OD_{600}$ and then boiling the cells in 0.02 M sodium hydroxide solution (0.02M NaOH). The DNA is then diluted and used as template for the qPCR reaction. The number of chromosomes carrying each of the evaluated loci is calculated according to the method described by Pavelka et al. For comparison, qPCR is performed on the yACV20 strain. Results are as indicated in FIGS. 1A-1C (where strain yACV20 is designated as "WT").

As shown in FIG. 1A, strains m38, m39 and m40 have only one copy of each of the tested loci, suggesting that one chromosome from each pair of chromosomes that carry these loci are present. These strains are likely haploids having N chromosomes.

Figure 1B:
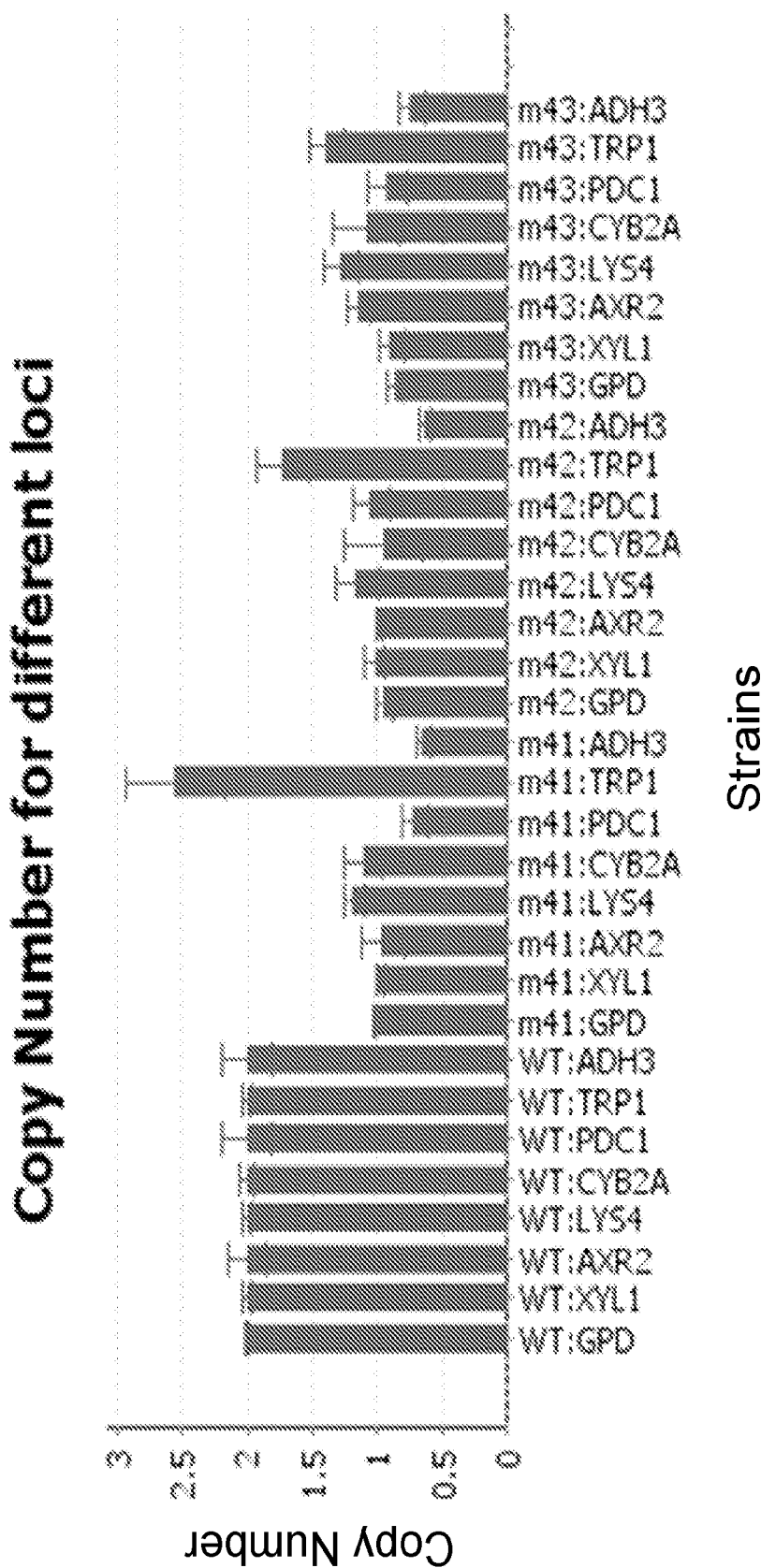
FIG. 1B is a graph showing the copy number at various loci for a control diploid strain and three less-than-diploid strains.

FIG. 1B shows that strain m43 has only one copy of each of the tested loci, and is a likely haploid having N chromosomes. Strains m41 and m42 have at least two copies of the TRP1 locus, but only one copy of each of the other loci, suggesting that this strain contains at least two copies of the chromosome carrying the TRP1 locus, but only one copy of each of the chromosomes carrying the other loci.

Figure 1C:
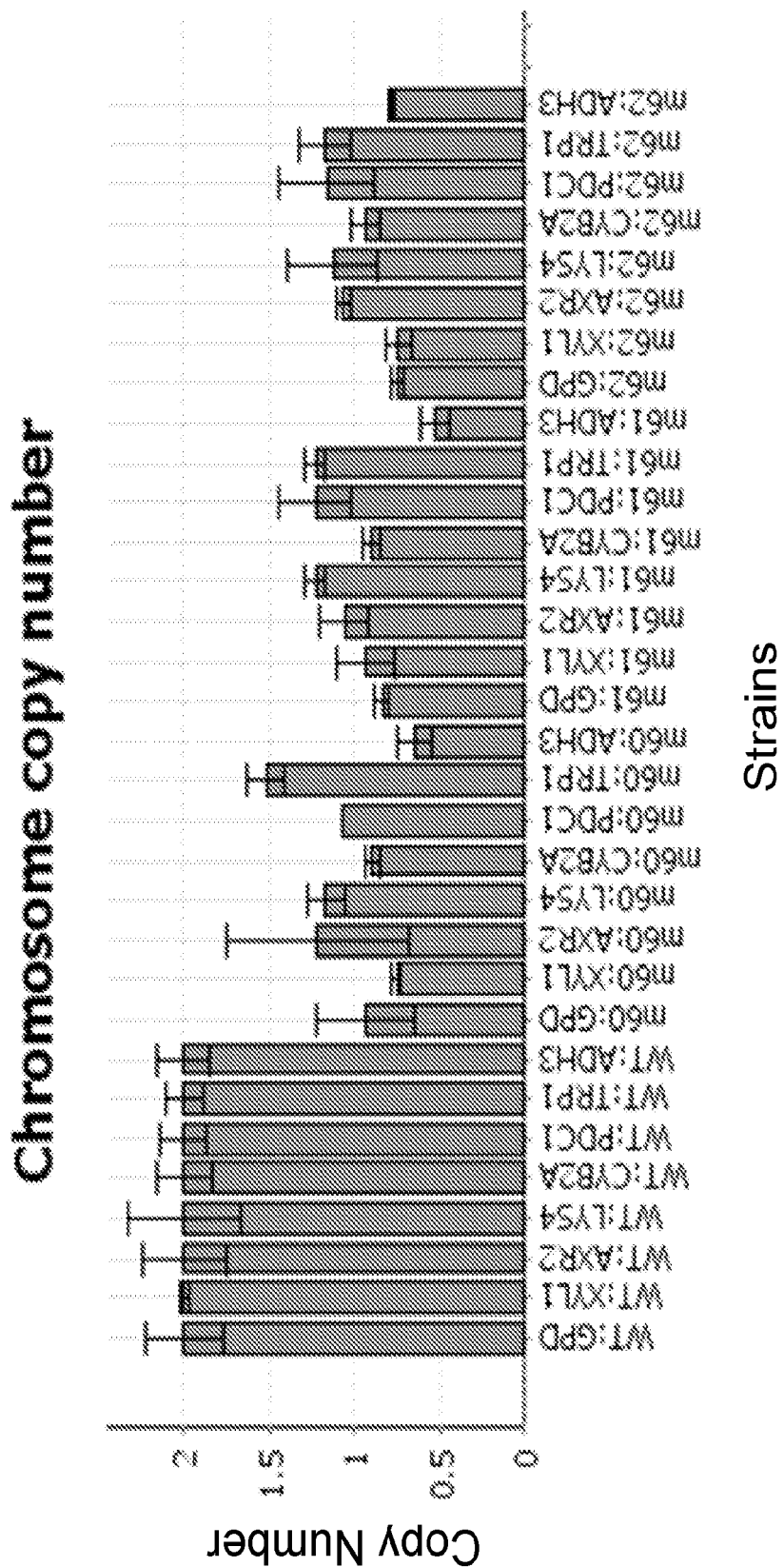
FIG. 1C is a graph showing the copy number at various loci for a control diploid strain and three less-than-diploid strains.

FIG. 1C shows that strains m60, m61 and m62 have only one copy of each of the tested loci, suggesting that one chromosome from each pair of chromosomes that carry these loci are present. These strains are likely haploids having N chromosomes.

To further confirm that strains m9, m12, m38, m39, m40, m41, m42, m43, m60, m61 and m62 are less-than-diploid, the ADE2 gene of each strain is deleted. The absence of the ADE2 gene is confirmed in each case by visual inspection of the colonies, as strains lacking the ADE2 gene turn pink when exposed to oxygen due to the buildup of the substrate of the ADE2 enzyme in the cells. Complete elimination of the ADE2 gene is accomplished in each case in a single transformation, which confirms that each of theses strains possesses only one copy of the ADE2 gene prior to performing the ADE2 deletion, and therefore only one member of the chromosome pair that carries that gene.

PCR is performed on m9 and m12 after the deletion of the ADE2 gene. Strain m9 shows a single copy of each SNP locus except the ADE2 gene locus, where no copies are found. Strain m12 shows a single copy of all loci except for the TRP1 gene, which appears in two copies, and the ADE2 gene, which is absent.

The DNA content of cells of colonies of known diploid strain yACV20 and cells of colonies of putative less-than-diploid strains m9, m20, m33, m37, m40 and m61 are measured by FACS on a BD Accuri C6 flow cytometer (BD Biosciences) equipped with a 533/30 filter in filter position FL-1 and a 488 nm laser. The cells are fixed in ethanol at −20 C for a minimum of 8 hours prior to processing and stained with Sytox Green fluorescent dye (Invitrogen). The intensity of the fluorescent light emitted from each cell is measured using FSC Express Version 4 software. The resulting histograms are shown in FIG. 2.

As shown in FIG. 2, the histogram corresponding to known diploid strain yACV20 exhibits two distinct fluorescence intensity peaks. The lower intensity peak exhibits a median intensity of about 466,000 in arbitrary units as defined by the software. This peak represents primarily diploid cells that are in the $G_0$ or $G_1$ gaps in the cell cycle. The higher intensity peak exhibits a median intensity of about 869,000 units. This peak represents cells that are undergoing mitosis and have duplicated their chromosomes as part of the mitotic process.

The histograms of strains m9, m20, m33, m37, m40 and m61 also exhibit two distinct peaks, the lower intensity peak again corresponding to cells in the $G_0$ and/or $G_1$ gaps of the cell cycle and the higher intensity peak corresponding to cells that are undergoing mitosis and have duplicated their chromosomes.

The median intensity of the lower intensity peaks of strains m9, m20, m33, m37, m40 and m61 all have values in the range of about 238,000 to 255,000 units, or approximately 51-57% of the intensity value of the lower intensity peak for the known diploid strain. The median intensity of the higher intensity peaks for these strains range from about 454,000 to 485,000, or 52-56% of the corresponding value for the known diploid peak. These results indicate that m9, m20, m33, m37, m40 and m61 are all less-than-diploid, and are all approximately haploid.

Figure 3A:
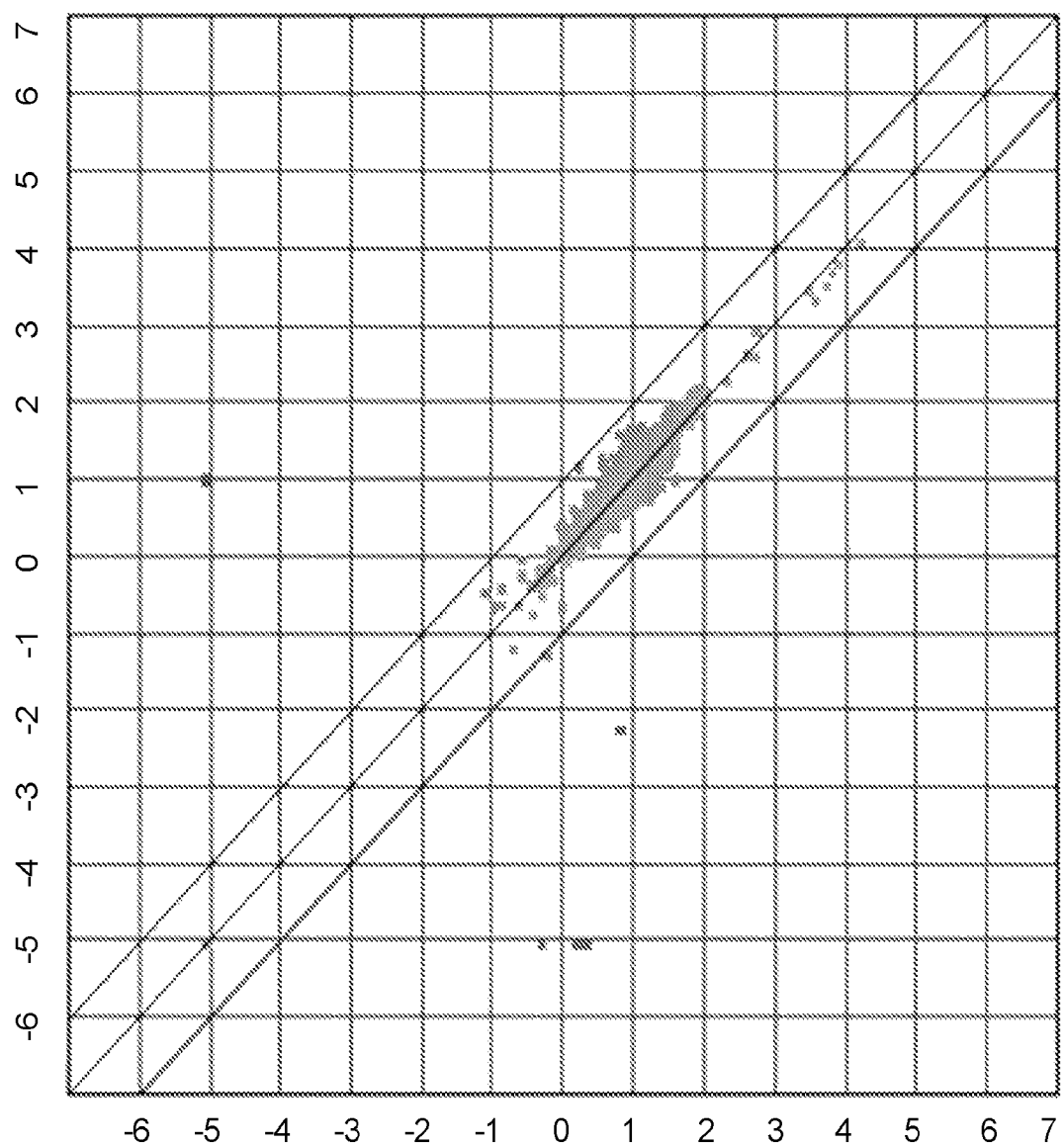
FIG. 3A is a read-depth comparison two known diploid strains.
Figure 3B:
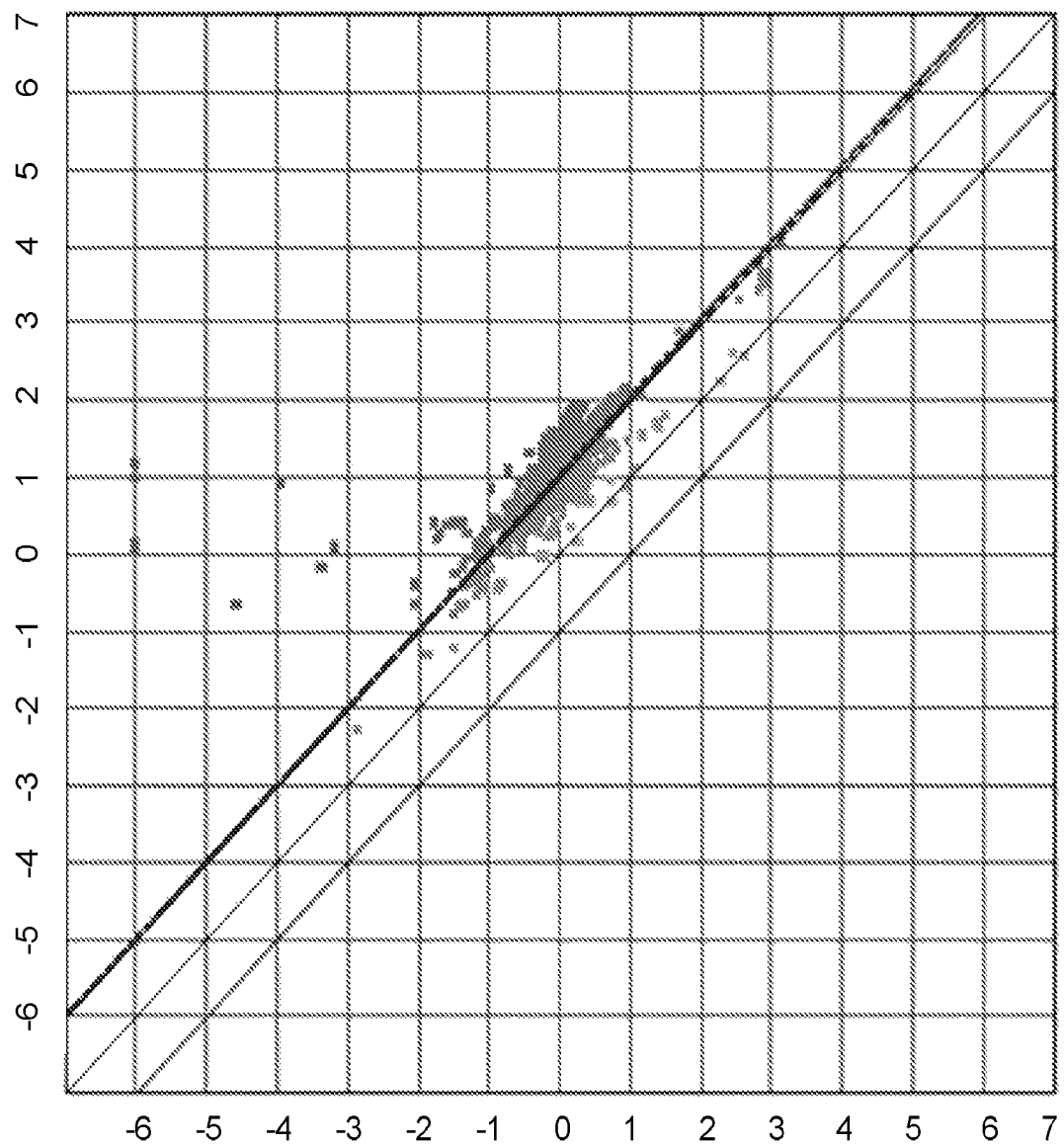
FIG. 3B is a read-depth comparison of a known diploid strain and a less-than-diploid strain of the invention.
Figure 3C:
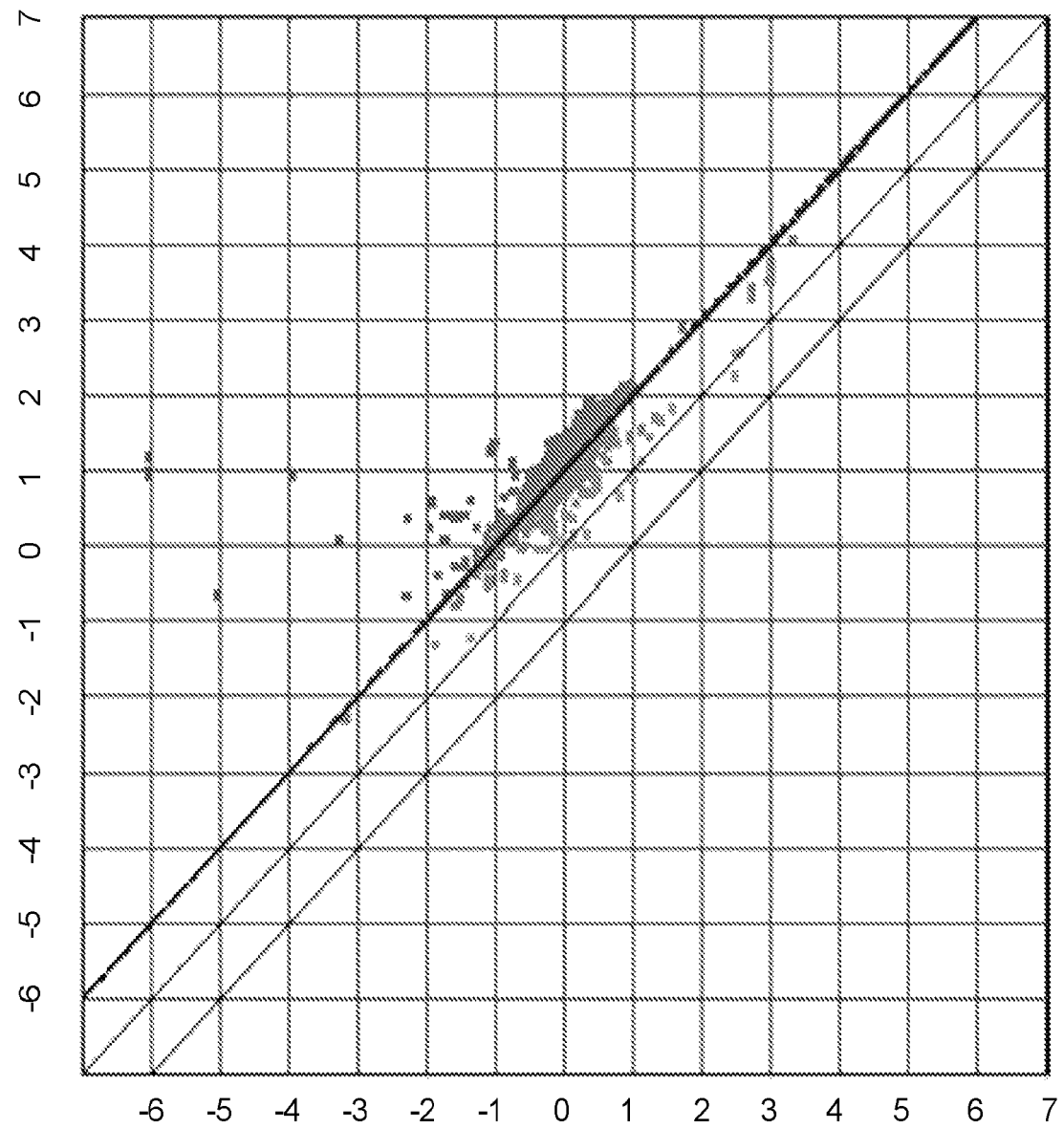
FIG. 3C is a read-depth comparison of a known diploid strain and a less-than-diploid strain of the invention.
Figure 3D:
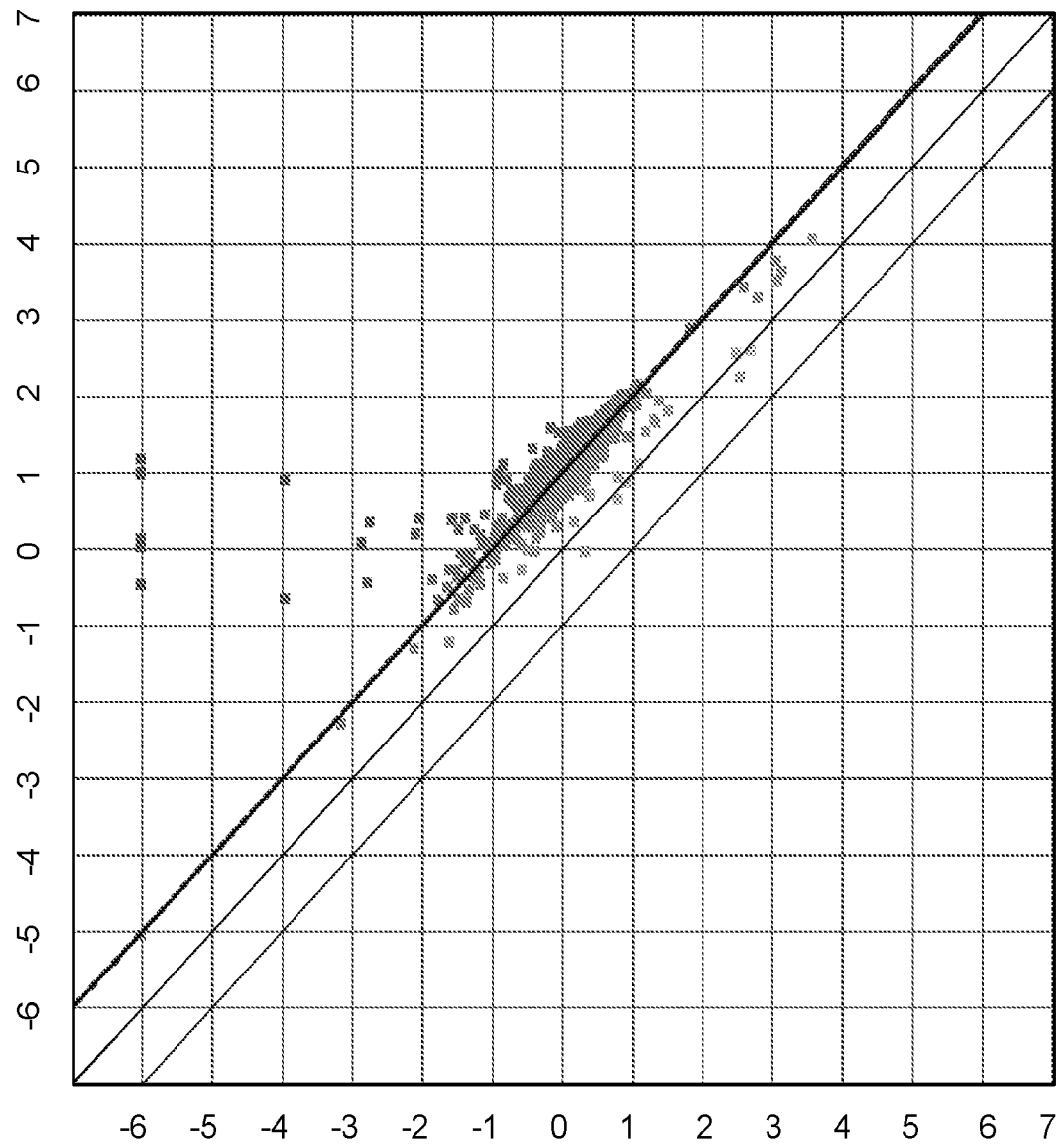
FIG. 3D is a read-depth comparison of a known diploid strain and a less-than-diploid strain of the invention.
Figure 3E:
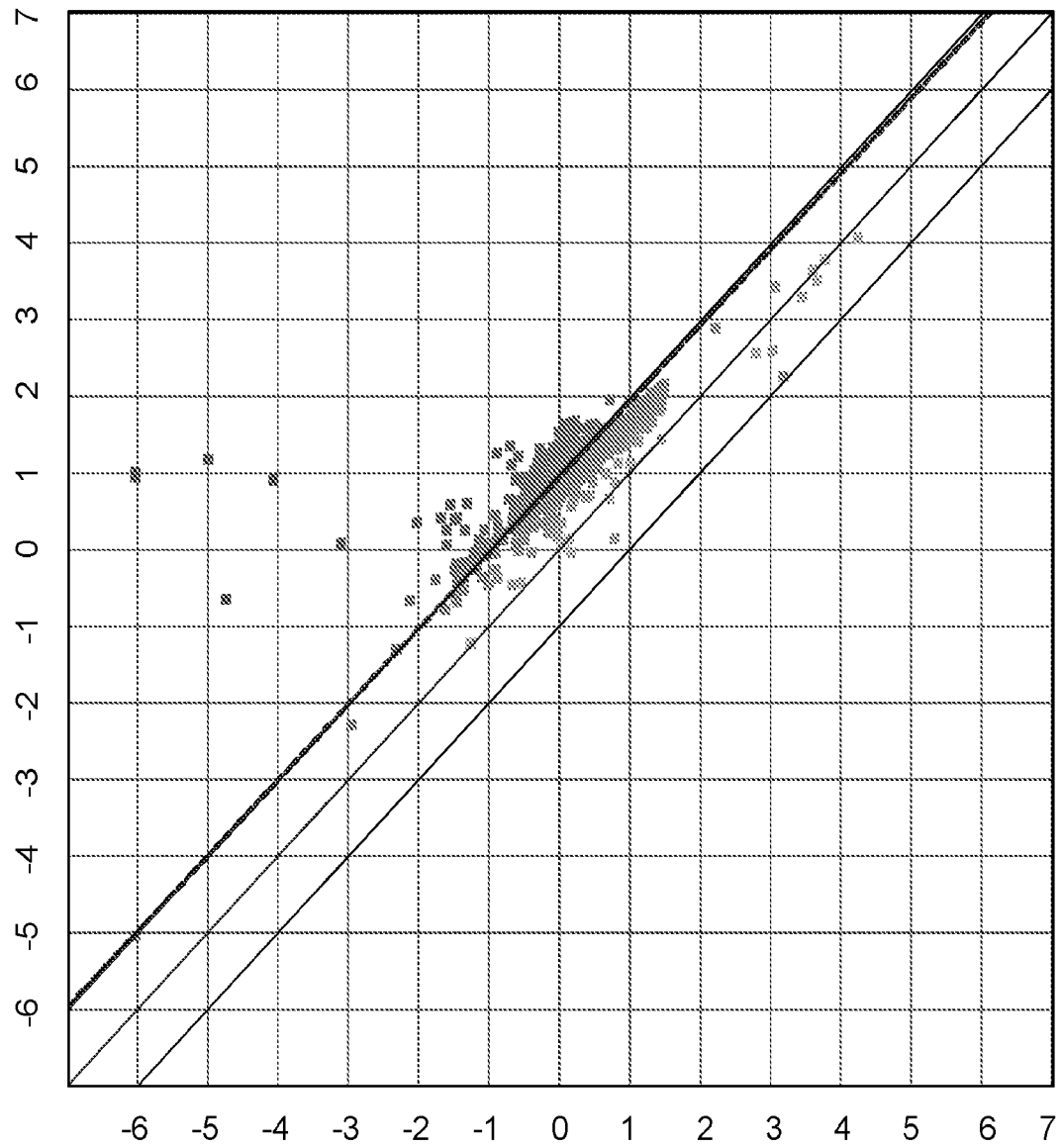
FIG. 3E is a read-depth comparison of a known diploid strain and a less-than-diploid strain of the invention.
Figure 3F:
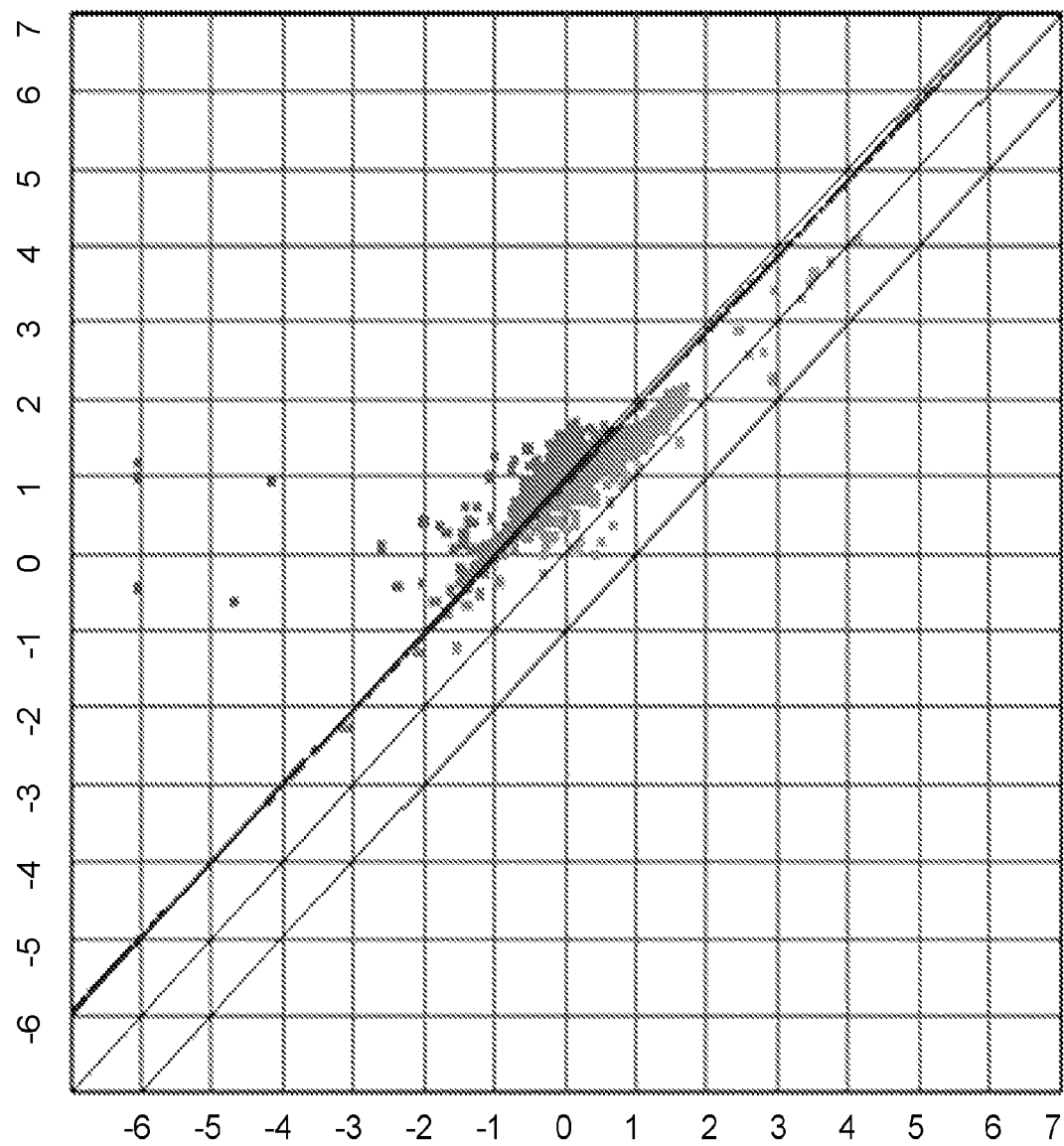
FIG. 3F is a read-depth comparison of a known diploid strain and a less-than-diploid strain of the invention.

The genomes of less-than-diploid strains m9, m33, m37, m40 and m61 are sequenced using Illumina hi-Seq NGS technology. The resultant data is then analyzed using DNA star software to compare the read depth of the genes in the genome. This comparison determines the copy number of the genes by comparing the data from two strains. Strains that are both diploid have equal numbers of all genes, which will result in an overall ratio of 1:1. This is shown in FIG. 3A, in which two diploid strains are evaluated. The three lines extending upwardly from lower left to upper right represent read depth ratios of 2:1, 1:1 and 1:2, respectively, from left to right. As seen in FIG. 3A, the data points fall closely along the 1:1 read depth line, as expected when two diploid strains are compared.

As shown in FIGS. 3B-3F, the data obtained by comparing strains m9, m33, m37, m40 and m61 with the known diploid strain falls closely along the line representing a 2:1 depth ratio. This data indicates the strains m9, m33, m37, m40 and m61 are approximately haploid.

EXAMPLE 2

A known diploid *I. orientalis* strain and less-than-diploid strains m9, m33, m37, m40, m43 and m61 are evaluated for growth in various YPD media. Each strain is grown up overnight in tubes in 3 mL of YPD at 30° C. The $OD_{600}$ of each of the cultures is measured. The cultures are then diluted to $OD_{600}$ 0.05 in 1 mL of the respective media. 125 μL volume of each diluted culture is added to the wells in a 96-well plate. The strains tested in each medium are run in triplicate and the results averaged. Plates were incubated at 30° C.

The plates are read every 30 minutes for the first 3 hours and then read every hour after that.

Growth is tested in the following media: YDP at pH 7; YPD at pH 3.0; YPD+50 g/L lactic acid at pH 2.97; YPD+50 g/L succinic acid at pH 3.0; and YPD+65 g/L 3-hydroxy-propionic acid at pH 3.3. Results are as indicated in the following table.

| Medium | Growth Rate (UNITS) | | | | |
| --- | --- | --- | --- | --- | --- |
| | Wild-type strain | m9 | m40 | m43 | m61 |
| YPD pH 7 | 0.76 | 0.71 | 0.69 | 0.67 | 0.70 |
| YPD pH 3 | 0.61 | 0.48 | 0.55 | 0.49 | 0.51 |
| YPD + lactic acid pH 3.0 | 0.26 | 0.26 | 0.28 | 0.21 | 0.22 |
| YPD + Succinic Acid pH 2.97 | 0.50 | 0.39 | 0.51 | 0.38 | 0.53 |
| YPD + 3HP pH 3.3 | 0.15 | 0.08 | 0.15 | 0.10 | 0.11 |

The less-than-diploid *I. orientalis* exhibit growth rates comparable or at most slightly diminished with respect to the growth rates of the diploid strain in all of these media.

EXAMPLE 3

The hygromycin marker in strain m33 is looped out using the Cre-Lox recombinase system. Loss of the marker is confirmed by PCR. This strain is designated strain yAN58. The MATα locus of a strain yAN58 cell (SEQ. ID. NO. 2) is replaced with a cassette that contains the MATα gene (SEQ. ID. NO. 1) and a URA3 marker gene to create strain yAN70. Strain yAN70 is grown in a 5-fluororitic acid medium to select for cells that have lost the URA 3 marker gene. The resulting strain is designated strain yACV42.

Strain yAN58 and strain yACV42 each is engineered to replace the native pyruvate decarboxylase (PDC1) gene with a *I. helveticus* LDH gene using methods as described in WO 2007/032792. Successful transformants are confirmed by PCR. They are designated yAN58L and yACV42L.

The URA3 marker gene is introduced into yACV42L cells. The HIS auxotrophy is restored to cells from strain yAN58L. The resulting transformed yACV42L and strain yAN58L cells are grown together on a yeast plus dextrose plates at room temperature for 24 hours. Mating is confirmed by replica plating to ScD-Ura-HIS plates. Diploid cells that are HIS+ and URA+ grow on the ScD-Ura-HIS plates and are isolated. These cells are designated Diploid 42/58.

Strains m33, yAn58L, yACV42L and Diploid 42/58 are cultivated separately in DM medium in shake flasks for 90 hours. The DM medium contains 5 g/L ammonium sulfate, around 3 g/L potassium dihydrogen phosphate, amend 0.5 g/L magnesium sulfate, trace elements, vitamins and 55 g/L glucose. Final glucose and lactic acid titers and yield on glucose are determined in each case. For comparison, two known diploid *I. orientalis*, in which both PDC1 alleles have been deleted and replaced with the same LDH gene, is cultivated under the same conditions.

All of the strains consume 80-90 g/L of glucose in 96 hours. All produce 60-70 g/L of lactate in the same time, for yields in each case of 73-77%. The haploids, and diploids made by mating the haploids, perform very similarly to cells produced by replacing the PDC1 genes of a known diploid with an LDH gene.

What is claimed is:

1. A method of making a viable Issatchenkia orientalis organism that contains N to 2N−1 chromosomes, comprising the steps of:
   a) growing parent diploid and/or tetraploid *I. orientalis* cells in the presence of an agent selected from the group consisting of nocodazole, benomyl, colchicine, para-fluoro-phenylalanine, and combinations thereof; and
   b) isolating and identifying at least a portion of the viable daughter cells that contain N to 2N−1 chromosomes, wherein 2N represents the number of chromosomes in wild-type *Issatchenkia orientalis*.

2. The method of claim 1 wherein the agent comprises benomyl.

3. The method of claim 1 wherein step b) includes the steps of i) growing *Issatchenkia orientalis* cells in the presence of a dye that differentially stains *Issatchenkia orientalis* cells having N to 2N−1 chromosomes and *Issatchenkia orientalis* cells having at least 2N chromosomes to form colonies of the stained cells and ii) identifying *Issatchenkia orientalis* colonies containing N to 2N−1 chromosomes on the basis of a difference in appearance due to the differential staining.

4. The method of claim 1 wherein step b) includes a step of staining viable daughter cells with a fluorescent tag, performing fluorescence-activated cell sorting, and identifying daughter cells having a peak intensity at least 20% lower than the peak intensity of a known diploid *Issatchenkia orientalis* cell.

5. The method of claim 1 wherein the diploid and/or tetraploid *Issatchenkia orientalis* includes at least one pair of chromosomes that are heterozygous at at least one locus and step b) includes a step of identifying daughter cells that are not heterozygous at said at least one locus.

6. The method of claim 5 wherein the diploid Issatchenkia orientalis cells and tetraploid *Issatchenkia orientalis* cells contain a heterozygous chromosome pair wherein one of the heterozygous chromosome pair includes a deletion or disruption of native gene that when deleted or disrupted confers resistance to a selection agent and the other of the heterozygous chromosome pair contains the native gene, and step b) includes a step of exposing daughter cells to the selection agent and identifying daughter cells that are resistant to the selection agent.

7. The method of claim 6 wherein the native gene that when deleted or disrupted confers resistance to a selection agent is a orotidine-5′-phosphate decarboxylase gene and the selection agent is 5-fluroorotic acid.

8. The method of claim 6 wherein the native gene that when deleted or disrupted confers resistance to a selection agent is a tryptophan synthase gene and the selection agent is 5-fluroanthranilic acid.

9. The method of claim 6 wherein the native gene that when deleted or disrupted confers resistance to a selection agent is an arginine permease gene and the selection agent is canavanine.

10. The method of claim 6 wherein the native gene that when deleted or disrupted confers resistance to a selection agent is a yeast ribosomal protein CYH2 gene and the selection agent is cycloheximide.

11. The method of claim 1 wherein at least one pair of chromosomes in the diploid and/or tetraploid *Issatchenkia orientalis* includes a single-nucleotide polymorphism and step b) includes a step of identifying daughter cells that do not contain the single-nucleotide polymorphism.

12. The method of claim 1, wherein the viable daughter cells identified and isolated in step b) contain N to N+2 chromosomes, wherein the 2N represents the number of chromosomes in wild-type *Issatchenkia orientalis*.

13. The method of claim 1, wherein the viable daughter cells identified and isolated in step b) are haploid.

14. The method of claim 1, wherein the viable daughter cells identified and isolated in step b) produce on fluorescence-assisted cell sorting a fluorescence signal having an intensity that is 70 to 80% of the intensity produced by a diploid *Issatchenkia orientalis* cell having 2N chromosomes.

15. The method of claim 1, wherein the viable daughter cells identified and isolated in step b) produce on fluorescence-assisted cell sorting a fluorescence signal having an intensity that is 40 to 60% of the intensity produced by a diploid *Issatchenkia orientalis* cell having 2N chromosomes.

* * * * *